US008858553B2

(12) United States Patent
Chojin (10) Patent No.: US 8,858,553 B2
(45) Date of Patent: Oct. 14, 2014

(54) DIELECTRIC JAW INSERT FOR ELECTROSURGICAL END EFFECTOR

(75) Inventor: Edward M. Chojin, Boulder, CO (US)

(73) Assignee: Covidien LP, Mansfield, MA (US)

( * ) Notice: Subject to any disclaimer, the term of this patent is extended or adjusted under 35 U.S.C. 154(b) by 617 days.

(21) Appl. No.: 12/696,857

(22) Filed: Jan. 29, 2010

(65) Prior Publication Data
US 2011/0190765 A1    Aug. 4, 2011

(51) Int. Cl.
A61B 18/14 (2006.01)
A61B 17/295 (2006.01)
A61B 17/285 (2006.01)
A61B 17/28 (2006.01)
A61B 17/29 (2006.01)

(52) U.S. Cl.
CPC ..... *A61B 18/1445* (2013.01); *A61B 2017/2825* (2013.01); *A61B 17/295* (2013.01); *A61B 2017/2929* (2013.01); *A61B 17/285* (2013.01); *A61B 2017/2926* (2013.01)
USPC .............................................. 606/51; 606/52

(58) Field of Classification Search
USPC ................................. 606/27, 34, 41, 51, 52
See application file for complete search history.

(56) References Cited

U.S. PATENT DOCUMENTS

| | | | |
|---|---|---|---|
| 2,002,594 A | 5/1935 | Wappler et al. | |
| 4,041,952 A | 8/1977 | Morrison, Jr. et al. | |
| 5,151,102 A | 9/1992 | Kamiyama et al. | |
| 5,282,799 A | 2/1994 | Rydell | |
| 5,396,900 A | 3/1995 | Slater et al. | |
| 5,456,684 A | 10/1995 | Schmidt et al. | |
| 5,665,100 A | 9/1997 | Yoon | |
| 5,674,220 A | 10/1997 | Fox et al. | |
| 5,797,537 A | 8/1998 | Oberlin et al. | |
| 5,891,142 A * | 4/1999 | Eggers et al. | 606/51 |
| 5,951,549 A | 9/1999 | Richardson et al. | |
| 5,976,132 A | 11/1999 | Morris | |
| 5,984,938 A | 11/1999 | Yoon | |

(Continued)

FOREIGN PATENT DOCUMENTS

| | | |
|---|---|---|
| DE | 2415263 | 10/1975 |
| DE | 2514501 | 10/1976 |

(Continued)

OTHER PUBLICATIONS

European Search Report for European Application No. 11152360 dated Jun. 6, 2011.

(Continued)

*Primary Examiner* — Michael Peffley
*Assistant Examiner* — Daniel Fowler (57) ABSTRACT

The present disclosure relates to an end effector assembly for use with an electrosurgical instrument and methods of manufacturing the same. The end effector assembly includes a pair of opposing first and second jaw members and a jaw insert. Each of the opposing jaw members has a tissue contacting surface and one or more of the jaw members are monolithic. Additionally, at least one of the jaw members is moveable relative to the other from a first, open position to a second, closed position for grasping tissue. The monolithic jaw member also has a cavity defined therein. The jaw insert is selectively positionable within the cavity of the monolithic jaw member. The jaw insert includes a tissue contacting surface and a portion of the jaw insert includes a dielectric material configured to reduce the thermal mass of the monolithic jaw member.

20 Claims, 6 Drawing Sheets

(56) References Cited

U.S. PATENT DOCUMENTS

| | | | |
|---|---|---|---|
| 6,050,996 A * | 4/2000 | Schmaltz et al. | 606/51 |
| 6,113,598 A | 9/2000 | Baker | |
| 6,126,658 A | 10/2000 | Baker | |
| 6,162,220 A | 12/2000 | Nezhat | |
| 6,174,309 B1 | 1/2001 | Wrublewski et al. | |
| 6,273,887 B1 | 8/2001 | Yamauchi et al. | |
| 6,511,480 B1 * | 1/2003 | Tetzlaff et al. | 606/51 |
| 6,602,252 B2 | 8/2003 | Mollenauer | |
| 6,770,072 B1 * | 8/2004 | Truckai et al. | 606/52 |
| 7,083,618 B2 * | 8/2006 | Couture et al. | 606/51 |
| 7,329,257 B2 | 2/2008 | Kanehira et al. | |
| 7,887,536 B2 | 2/2011 | Johnson et al. | |
| 8,016,827 B2 | 9/2011 | Chojin | |
| 8,112,871 B2 | 2/2012 | Brandt et al. | |
| 8,114,122 B2 | 2/2012 | Nau, Jr. | |
| 8,133,254 B2 | 3/2012 | Dumbauld et al. | |
| 8,142,473 B2 | 3/2012 | Cunningham | |
| 8,162,965 B2 | 4/2012 | Reschke et al. | |
| 8,162,973 B2 | 4/2012 | Cunningham | |
| 8,197,479 B2 | 6/2012 | Olson et al. | |
| 8,226,650 B2 | 7/2012 | Kerr | |
| 8,251,994 B2 | 8/2012 | McKenna et al. | |
| 8,257,387 B2 | 9/2012 | Cunningham | |
| 8,266,783 B2 | 9/2012 | Brandt et al. | |
| 8,282,634 B2 | 10/2012 | Cunningham et al. | |
| 8,287,536 B2 | 10/2012 | Mueller et al. | |
| 8,292,886 B2 | 10/2012 | Kerr et al. | |
| 8,303,582 B2 | 11/2012 | Cunningham | |
| 8,317,787 B2 | 11/2012 | Hanna | |
| 8,323,310 B2 | 12/2012 | Kingsley | |
| 8,328,803 B2 | 12/2012 | Regadas | |
| 8,343,150 B2 | 1/2013 | Artale | |
| 8,343,151 B2 | 1/2013 | Siebrecht et al. | |
| 8,357,159 B2 | 1/2013 | Romero | |
| 8,388,647 B2 | 3/2013 | Nau, Jr. et al. | |
| 8,430,876 B2 | 4/2013 | Kappus et al. | |
| 8,439,911 B2 | 5/2013 | Mueller | |
| 8,469,956 B2 | 6/2013 | McKenna et al. | |
| 8,469,957 B2 | 6/2013 | Roy | |
| 8,486,107 B2 | 7/2013 | Hinton | |
| 8,512,371 B2 | 8/2013 | Kerr et al. | |
| 8,535,312 B2 | 9/2013 | Horner | |
| 8,568,412 B2 | 10/2013 | Brandt et al. | |
| 8,623,017 B2 | 1/2014 | Moses et al. | |
| 8,632,539 B2 | 1/2014 | Twomey et al. | |
| 8,632,564 B2 | 1/2014 | Cunningham | |
| 8,636,761 B2 | 1/2014 | Cunningham et al. | |
| 8,679,115 B2 | 3/2014 | Reschke | |
| 2003/0171747 A1 | 9/2003 | Kanehira et al. | |
| 2004/0078035 A1 | 4/2004 | Kanehira et al. | |
| 2004/0143263 A1 * | 7/2004 | Schechter et al. | 606/51 |
| 2005/0004569 A1 | 1/2005 | Witt et al. | |
| 2005/0113827 A1 * | 5/2005 | Dumbauld et al. | 606/45 |
| 2010/0049187 A1 | 2/2010 | Carlton et al. | |
| 2010/0057081 A1 | 3/2010 | Hanna | |
| 2010/0057082 A1 | 3/2010 | Hanna | |
| 2010/0057084 A1 | 3/2010 | Hanna | |
| 2010/0063500 A1 | 3/2010 | Muszala | |
| 2010/0069903 A1 | 3/2010 | Allen, IV et al. | |
| 2010/0069953 A1 | 3/2010 | Cunningham et al. | |
| 2010/0076427 A1 | 3/2010 | Heard | |
| 2010/0076430 A1 | 3/2010 | Romero | |
| 2010/0076431 A1 | 3/2010 | Allen, IV | |
| 2010/0249769 A1 | 9/2010 | Nau, Jr. et al. | |
| 2010/0274244 A1 | 10/2010 | Heard | |
| 2010/0280511 A1 | 11/2010 | Rachlin et al. | |
| 2011/0034918 A1 | 2/2011 | Reschke | |
| 2011/0054468 A1 | 3/2011 | Dycus | |
| 2011/0054471 A1 | 3/2011 | Gerhardt et al. | |
| 2011/0060335 A1 | 3/2011 | Harper et al. | |
| 2011/0071523 A1 | 3/2011 | Dickhans | |
| 2011/0077648 A1 | 3/2011 | Lee et al. | |
| 2012/0042143 A1 | 2/2012 | Shimizu et al. | |

FOREIGN PATENT DOCUMENTS

| | | |
|---|---|---|
| DE | 2627679 | 1/1977 |
| DE | 3423356 | 6/1986 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 10045375 | 10/2002 |
| DE | 202007016233 | 1/2008 |
| DE | 19738457 | 1/2009 |
| EP | 0509670 | 10/1992 |
| EP | 0853922 | 7/1998 |
| EP | 1159926 | 12/2001 |
| EP | 1330991 | 7/2003 |
| EP | 1 532 933 | 5/2005 |
| JP | 61-501068 | 9/1984 |
| JP | 65-502328 | 3/1992 |
| JP | 5-5106 | 1/1993 |
| JP | 5-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09010223 | 1/1997 |
| JP | 11-070124 | 5/1998 |
| JP | 2000-102545 | 9/1998 |
| JP | 11244298 | 9/1999 |
| JP | 2000-342599 | 12/2000 |
| JP | 2000-350732 | 12/2000 |
| JP | 2001-008944 | 1/2001 |
| JP | 2001-029356 | 2/2001 |
| JP | 2001-128990 | 5/2001 |
| SU | 401367 | 11/1974 |
| WO | WO 96/11635 | 4/1996 |
| WO | WO 96/22056 | 7/1996 |
| WO | WO 00/36986 | 6/2000 |
| WO | WO 00/47124 | 8/2000 |
| WO | WO 01/54604 | 8/2001 |
| WO | WO 2005/110264 | 11/2005 |

OTHER PUBLICATIONS

U.S. Appl. No. 12/336,970 dated Dec. 17, 2008 inventor: Sremcich et al.
U.S. Appl. No. 12/176,679, filed Jul. 21, 2008.
U.S. Appl. No. 12/192,170, filed Aug. 15, 2008.
U.S. Appl. No. 12/192,189, filed Aug. 15, 2008.
U.S. Appl. No. 12/192,243, filed Aug. 15, 2008.
U.S. Appl. No. 12/195,624, filed Aug. 21, 2008.
U.S. Appl. No. 12/200,154, filed Aug. 28, 2008.
U.S. Appl. No. 12/200,246, filed Aug. 28, 2008.
U.S. Appl. No. 12/200,396, filed Aug. 28, 2008.
U.S. Appl. No. 12/200,526, filed Aug. 28, 2008.
U.S. Appl. No. 12/204,976, filed Sep. 5, 2008.
U.S. Appl. No. 12/210,598, filed Sep. 15, 2008.
U.S. Appl. No. 12/211,205, filed Sep. 16, 2008.
U.S. Appl. No. 12/233,157, filed Sep. 18, 2008.
U.S. Appl. No. 12/236,666, filed Sep. 24, 2008.
U.S. Appl. No. 12/237,515, filed Sep. 25, 2008.
U.S. Appl. No. 12/237,556, filed Sep. 25, 2008.
U.S. Appl. No. 12/237,582, filed Sep. 25, 2008.
U.S. Appl. No. 12/244,873, Oct. 3, 2008.
U.S. Appl. No. 12/246,553, filed Oct. 7, 2008.
U.S. Appl. No. 12/248,104, filed Oct. 9, 2008.
U.S. Appl. No. 12/248,115, filed Oct. 9, 2008.
U.S. Appl. No. 12/254,123, filed Oct. 20, 2008.
U.S. Appl. No. 12/331,643, filed Dec. 10, 2008.
U.S. Appl. No. 12/336,970, filed Dec. 17, 2008.
U.S. Appl. No. 12/352,942, filed Jan. 13, 2009.
U.S. Appl. No. 12/353,466, filed Jan. 14, 2009.

(56) References Cited

OTHER PUBLICATIONS

U.S. Appl. No. 12/353,470, filed Jan. 14, 2009.
U.S. Appl. No. 12/353,474, filed Jan. 14, 2009.
U.S. Appl. No. 12/363,086, filed Jan. 30, 2009.
U.S. Appl. No. 12/410,195, filed Mar. 24, 2009.
U.S. Appl. No. 12/411,542, filed Mar. 26, 2009.
U.S. Appl. No. 12/419,729, filed Apr. 7, 2009.
U.S. Appl. No. 12/429,533, filed Apr. 24, 2009.
U.S. Appl. No. 12/434,382, filed May 1, 2009.
U.S. Appl. No. 12/503,256, filed Jul. 15, 2009.
U.S. Appl. No. 12/508,052, filed Jul. 23, 2009.
U.S. Appl. No. 12/535,869, filed Aug. 5, 2009.
U.S. Appl. No. 12/543,831, filed Aug. 19, 2009.
U.S. Appl. No. 12/543,969, filed Aug. 19, 2009.
U.S. Appl. No. 12/548,031, filed Aug. 26, 2009.
U.S. Appl. No. 12/548,534, filed Aug. 27, 2009.
U.S. Appl. No. 12/548,566, filed Aug. 27, 2009.
U.S. Appl. No. 12/551,944, filed Sep. 1, 2009.
U.S. Appl. No. 12/553,509, filed Sep. 3, 2009.
U.S. Appl. No. 12/556,025, filed Sep. 9, 2009.
U.S. Appl. No. 12/556,407, filed Sep. 9, 2009.
U.S. Appl. No. 12/556,427, filed Sep. 9, 2009.
U.S. Appl. No. 12/556,796, filed Sep. 10, 2009.
U.S. Appl. No. 12/562,281, filed Sep. 18, 2009.
U.S. Appl. No. 12/565,281, filed Sep. 23, 2009.
U.S. Appl. No. 12/568,199, filed Sep. 28, 2009.
U.S. Appl. No. 12/568,282, filed Sep. 28, 2009.
U.S. Appl. No. 12/569,395, filed Sep. 29, 2009.
U.S. Appl. No. 12/569,710, filed Sep. 29, 2009.
U.S. Appl. No. 12/574,001, filed Sep. 6, 2009.
U.S. Appl. No. 12/574,292, filed Oct. 6, 2009.
U.S. Appl. No. 12/576,380, filed Oct. 9, 2009.
U.S. Appl. No. 12/607,191, filed Oct. 28, 2009.
Michael Choti, "Abdominoperineal Resection with the LigaSure Vessel Sealing System and LigaSure Atlas 20 cm Open Instrument"; Innovations That Work, Jun. 2003.
Chung et al., "Clinical Experience of Sutureless Closed Hemorrhoidectomy with LigaSure" Diseases of the Colon & Rectum vol. 46, No. 1 Jan. 2003.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicolectomy Using the LigaSure Vessel Sealing System" Innovations That Work, Sep. 1999.
Kennedy et al. "High-burst-strength, feedback-controlled bipolar vessel sealing". Surgical Endoscopy (1998) 12: 876-878.
Carus et al., "Initial Experience With the LigaSure Vessel Sealing System in Abdominal Surgery" Innovations That Work, Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J.Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Sayfan et al. "Sutureless Closed Hemorrhoidectomy: A New Technique" Annals of Surgery vol. 234 No. 1 Jul. 2001; pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. " Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.

(56) References Cited

OTHER PUBLICATIONS

McLellan et al. "Vessel Sealing for Hemostasis During Gynecologic Surgery" Sales/Product Literature 1999.
Int'l Search Report EP 98944778.4 dated Oct. 31, 2000.
Int'l Search Report EP 98957771 dated Aug. 9, 2001.
Int'l Search Report EP 98958575.7 dated Sep. 20, 2002.
Int'l Search Report EP 04013772.1 dated Apr. 1, 2005.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04752343.6 dated Jul. 20, 2007.
Int'l Search Report EP 05002671.5 dated Dec. 22, 2008.
Int'l Search Report EP 05002674.9 dated Jan. 16, 2009.
Int'l Search Report EP 05013463.4 dated Oct. 7, 2005.
Int'l Search Report EP 05013895.7 dated Oct. 21, 2005.
Int'l Search Report EP 05016399.7 dated Jan. 13, 2006.
Int'l Search Report EP 05017281.6 dated Nov. 24, 2005.
Int'l Search Report EP 05019130.3 dated Oct. 27, 2005.
Int'l Search Report EP 05019429.9 dated May 6, 2008.
Int'l Search Report EP 05020665.5 dated Feb. 27, 2006.
Int'l Search Report EP 05020666.3 dated Feb. 27, 2006.
Int'l Search Report EP 05021197.8 dated Feb. 20, 2006.
Int'l Search Report EP 05021779.3 dated Feb. 2, 2006.
Int'l Search Report EP 05021780.1 dated Feb. 23, 2006.
Int'l Search Report EP 05021937.7 dated Jan. 23, 2006.
Int'l Search Report—extended—EP 05021937.7 dated Mar. 15, 2006.
Int'l Search Report EP 05023017.6 dated Feb. 24, 2006.
Int'l Search Report EP 06002279.5 dated Mar. 30, 2006.
Int'l Search Report EP 06005185.1 dated May 10, 2006.
Int'l Search Report EP 06006716.2 dated Aug. 4, 2006.
Int'l Search Report EP 06008515.6 dated Jan. 8, 2009.
Int'l Search Report EP 06008779.8 dated Jul. 13, 2006.
Int'l Search Report EP 06014461.5 dated Oct. 31, 2006.
Int'l Search Report EP 06020574.7 dated Oct. 2, 2007.
Int'l Search Report EP 06020583.8 dated Feb. 7, 2007.
Int'l Search Report EP 06020584.6 dated Feb. 1, 2007.
Int'l Search Report EP 06020756.0 dated Feb. 16, 2007.
Int'l Search Report EP 06 024122.1 dated Apr. 16, 2007.
Int'l Search Report EP 06024123.9 dated Mar. 6, 2007.
Int'l Search Report EP 07 001480.8 dated Apr. 19, 2007.
Int'l Search Report EP 07 001488.1 dated Jun. 5, 2007.
Int'l Search Report EP 07 009026.1 dated Oct. 8, 2007.
Int'l Search Report Extended—EP 07 009029.5 dated Jul. 20, 2007.
Int'l Search Report EP 07 009321.6 dated Aug. 28, 2007.
Int'l Search Report EP 07 010672.9 dated Oct. 16, 2007.
Int'l Search Report EP 07 013779.9 dated Oct. 26, 2007.
Int'l Search Report EP 07 014016 dated Jan. 28, 2008.
Int'l Search Report EP 07 015191.5 dated Jan. 23, 2008.
Int'l Search Report EP 07 015601.3 dated Jan. 4, 2008.
Int'l Search Report EP 07 020283.3 dated Feb. 5, 2008.
Int'l Search Report EP 07 021646.0 dated Mar. 20, 2008.
Int'l Search Report EP 07 021646.0 dated Jul. 9, 2008.
Int'l Search Report EP 07 021647.8 dated May 2, 2008.
Int'l Search Report EP 08 002692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 003813.4 dated Aug. 3, 2009.
Int'l Search Report EP 09 004491.8 dated Sep. 9, 2009.
Int'l Search Report EP 09 005575.7 dated Sep. 9, 2009.
Int'l Search Report EP 09 152267.2 dated Jun. 15, 2009.
Int'l Search Report EP 09 152898.4 dated Jun. 10, 2009.
Int'l Search Report EP 09 154850.3 dated Jul. 20, 2009.
Int'l Search Report EP 09 160476.9 dated Aug. 4, 2009.
Int'l Search Report EP 09 164903.8 dated Aug. 21, 2009.
Int'l Search Report PCT/US98/18640 dated Jan. 29, 1999.
Int'l Search Report PCT/US98/23950 dated Jan. 14, 1999.
Int'l Search Report PCT/US98/24281 dated Feb. 22, 1999.
Int'l Search Report PCT/US99/24869 dated Feb. 3, 2000.
Int'l Search Report PCT/US01/11218 dated Aug. 14, 2001.
Int'l Search Report PCT/US01/11224 dated Nov. 13, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/US03/28534 dated Dec. 19, 2003.
Int'l Search Report PCT/US04/03436 dated Mar. 3, 2005.
Int'l Search Report PCT/US04/13273 dated Dec. 15, 2004.
Int'l Search Report PCT/US04/15311 dated Jan. 12, 2005.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
Japanese Office Action dated May 7, 2014 issued in Japanese Application No. 2011-017305.

* cited by examiner

DIELECTRIC JAW INSERT FOR ELECTROSURGICAL END EFFECTOR

BACKGROUND

1. Technical Field

The present disclosure relates to varying sealing characteristics of a bipolar electrosurgical instrument with a monolithic jaw member. More particularly, the present disclosure relates to varying sealing characteristics by using a dielectric insert within a monolithic jaw member.

2. Description of Related Art

Open or endoscopic electrosurgical forceps utilize both mechanical clamping action and electrical energy to effect hemostasis. The electrode of each opposing jaw member is charged to a different electric potential such that when the jaw members grasp tissue, electrical energy can be selectively transferred through the tissue. Many times monolithic jaw members having a one-piece metallic configuration are utilized during such procedures. The monolithic jaw configuration allows for an efficient and easier manufacturing process, since fewer parts are needed to assemble a single jaw member.

Additionally, certain types of open and endoscopic electrosurgical forceps, as mentioned above, utilize a movable knife or cutting element that is movable via a cutting channel. Cutting channel is defined by a jaw member and is often characterized as a narrow cavity within one or both jaw members. Throughout a typical surgical procedure, various conductive fluids, for example, blood or saline may fill the cutting channel of a jaw member. Since the entire depth of the cutting channel is part of the electrical circuit in this type of jaw, material in the blade slot may become subject to the electrosurgical effect and may affect a cycle and/or a quality of a tissue seal. When this or similar situations occur, unnecessary complications arise for the user during a surgical procedure.

SUMMARY

The present disclosure relates to an end effector assembly for use with an electrosurgical instrument. The end effector assembly includes a pair of opposing first and second jaw members and a jaw insert. Each of the opposing jaw members has a tissue contacting surface and one or more of the jaw members are monolithic. Additionally, at least one of the jaw members is moveable relative to the other from a first, open position to a second, closed position for grasping tissue. The monolithic jaw member also has a cavity defined therein. The jaw insert is selectively positionable within the cavity of the monolithic jaw member. The jaw insert includes a tissue contacting surface and a portion of the jaw insert includes a dielectric material configured to reduce the thermal mass of the monolithic jaw member.

In embodiments, the jaw insert may define a cutting channel therealong configured to receive a cutting element therealong. The jaw insert may include a portion of conductive material that is configured to conduct electrosurgical energy received from the electrosurgical energy source. The jaw insert may also be overmolded to the monolithic jaw member. In embodiments, the jaw insert may include one or more mechanical interfaces that cooperate with corresponding mechanical interfaces to selectively position the jaw insert within the cavity. The mechanical interfaces may include one or more biasing members.

In embodiments, the tissue contacting surface of the at least one monolithic jaw member and the tissue contacting surface of the jaw insert may be offset relative to one another. Additionally, the tissue contacting surface of the jaw insert may be raised relative to the tissue contacting surface of the monolithic jaw member to form a gap between the monolithic jaw member and the opposing jaw member in the range of about 0.001 inches to about 0.006 inches. The jaw insert may be removable from the cavity.

The present disclosure also relates to a method of manufacturing an end effector assembly for use with an electrosurgical instrument. The method includes a step of fabricating opposing jaw members, at least one jaw member being monolithic and having a cavity defined therein. In another step, a jaw insert is fabricated having a portion including a dielectric material configured to reduce the thermal mass of the monolithic jaw member. In another step, the jaw insert is positioned within the cavity of the monolithic jaw member.

In other embodiments, the method includes the step of fabricating the jaw insert to define a cutting channel configured to receive a cutting element therealong. In another step, the jaw insert may be fabricated to include a portion of conductive material configured to conduct electrosurgical energy received from the electrosurgical energy source. In another step, the jaw insert is overmolded and positioned within the cavity of the monolithic jaw member. In another step, the jaw insert may be fabricated to include one or more mechanical interfaces that cooperate with a corresponding mechanical interface disposed within the cavity. In another step, a tissue contacting surface of the monolithic jaw member may be offset from a tissue contacting surface of the jaw insert.

BRIEF DESCRIPTION OF THE DRAWINGS

Various embodiment of the subject instrument are described herein with reference to the drawings wherein.

DETAILED DESCRIPTION

Embodiments of the presently-disclosed electrosurgical instrument are described in detail with reference to the drawings wherein like reference numerals identify similar or identical elements. As used herein, the term "distal" refers to that portion which is further from a user while the term "proximal" refers to that portion which is closer to a user. As used herein, the term "monolithic jaw member" refers to a jaw member of an end effector for a bipolar electrosurgical device having a one-piece configuration. More specifically, a major portion of the jaw member, including the electrode surface (e.g., a sealing surface) is machined from a one-piece conductive material, for example, but not limited to stainless steel. When the monolithic jaw member is configured to have a cutting channel, the cutting channel is machined (e.g., bored) into and along the length of the jaw member such that a cutting element may travel therethrough.

The present disclosure relates to modifying sealing characteristics of monolithic jaw members by embedding a dielectric jaw insert within the monolithic jaw members of the end effector assembly. The dielectric jaw insert modifies the seal area and thermal mass of the end effector by allowing the combination of materials in the structure to be altered. Additionally, the dielectric jaw insert can contain features such as a cutting channel to allow a cutting element to pass therethrough. In this manner, the cutting channel is electrically insulated from the monolithic jaw member such that fluids that are trapped in the cutting channel are not subject to the electrosurgical effect. The dielectric jaw inserts may be a discrete part separate from the end effector assembly or, in the alternative, may be molded into the monolithic jaw members during a manufacturing step. All of these novel features will be described in greater detail further below.

Figure 1A:
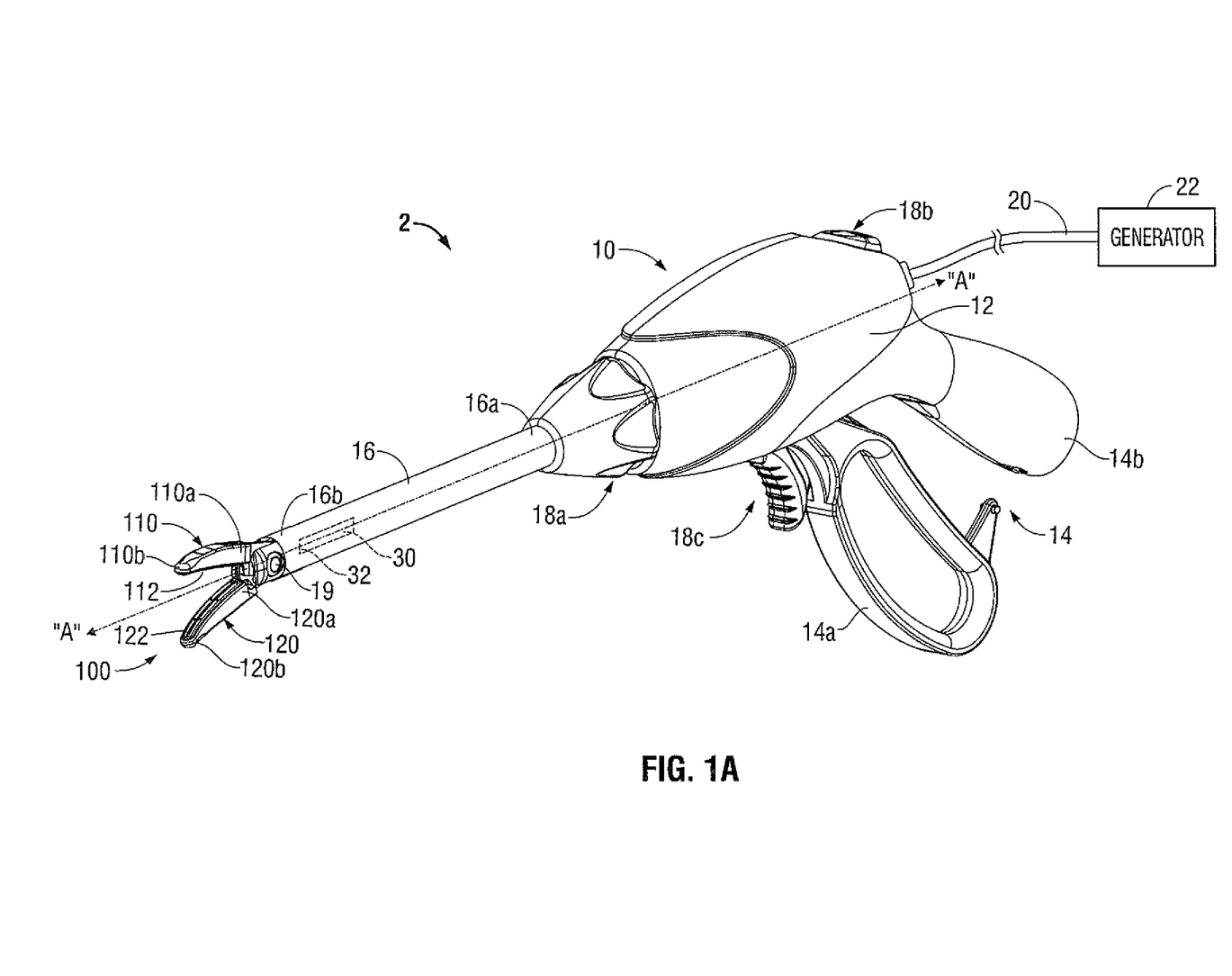
FIG. 1 is a perspective view of an endoscopic forceps for electrosurgical treatment having an end effector assembly in accordance with an embodiment of the present disclosure.
Figure 1B:
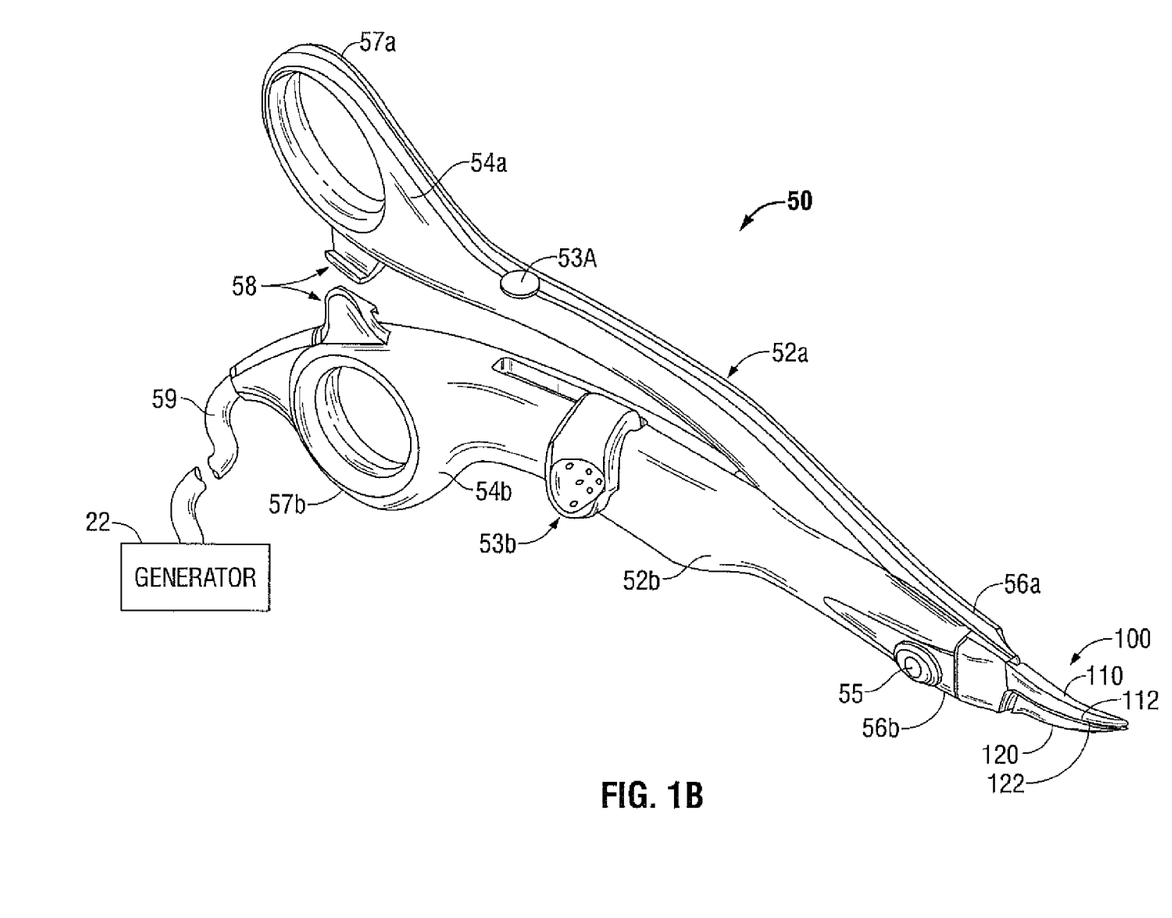

Referring now to the figures, FIG. 1A depicts a forceps 10 used in correlation with endoscopic surgical procedures and FIG. 1B depicts an open forceps 50 used in correlation with more traditional open surgical procedures. For the purposes herein, either an endoscopic instrument or an open instrument may be utilized with the cutting assembly described herein. It should be noted that different electrical and mechanical connections and considerations apply to each particular type of instrument. However, the novel aspects, with respect to the cutting assembly and its operating characteristics, remain generally consistent with respect to both the endoscopic or open designs.

Turning now to FIG. 1A, a tissue treatment system 2 according to the present disclosure is shown including a forceps 10 coupled to an electrosurgical energy source 22. Forceps 10 is particularly adapted to seal tissue using radiofrequency (RF) however, other types of suitable energy, for example, but not limited to light energy and microwave energy may be utilized to electrosurgically treat tissue. Energy source 22 is configured to output various types of energy such as RF energy (e.g., from about 300 MHz to about 5000 MHz). In addition, where laser energy is used, the energy source 22 may be a light source. If ultrasonic energy is desired, the energy source 22 may be adapted to provide an electrical excitation signal to one or more ultrasonic transducers within forceps 10. Forceps 10 is coupled to the energy source 22 via a cable 20 adapted to transmit the appropriate energy and control signals therebetween. Various embodiments of forceps 10 utilizing the aforementioned types of energy are discussed in more detail below.

Forceps 10 is configured to support an end effector assembly 100. Forceps 10 typically includes various conventional features (e.g., a housing 12, a handle assembly 14, a rotating assembly 18a and a trigger assembly 18b) which enable forceps 10 and end effector assembly 100 to mutually cooperate to grasp, seal and/or divide tissue grasped therebetween. Forceps 10 generally includes housing 12 and handle assembly 14 that includes moveable handle 14a and a fixed handle 14b which is integral with housing 12. Handle 14a is moveable relative to handle 14b to actuate end effector assembly 100 to grasp tissue. Forceps 10 also includes shaft 16 that has distal end 16b that mechanically engages end effector assembly 100 and proximal end 16a that mechanically engages housing 12 proximate rotating assembly 18a disposed at the distal end of housing 12. Rotating assembly 18a is mechanically associated with shaft 16. Movement of rotating assembly 18a imparts similar rotational movement to shaft 16 which, in turn, rotates end effector assembly 100.

End effector assembly 100 includes two jaw members 110 and 120 having proximal ends 110a, 120a and distal ends 110b, 120b, respectively. One or both jaw members 110 and 120 are pivotable about a pivot pin 19 and are movable from a first position wherein jaw members 110 and 120 are spaced relative to another, to a second position wherein jaw members 110 and 120 are closed and cooperate to grasp tissue therebetween. That is, jaw members 110 may have a unilateral configuration (e.g., only one jaw member is movable) and/or a bilateral configuration (e.g., both jaw members are movable). As discussed in more detail below, the end effector assembly 100 may include a removable dielectric insert.

A switch assembly 18b is configured to selectively provide electrical energy to the end effector assembly 100. More particularly, switch assembly 18b is configured to selectively supply electrical energy to tissue contacting surfaces 112 and 122 of jaw member 110 and 120, respectively. Cable 20 connects the forceps 10 to a source of electrosurgical energy 22, for example, but not limited to, an electrosurgical generator. Cable 20 is internally divided (not shown) within the handle assembly 14 and the shaft 16 to transport electrosurgical energy through various conductive paths and ultimately to end effector assembly 100. In this manner, the end effector assembly 100 may electrosurgically treat tissue.

In addition to switch assembly 18b, forceps 10 also includes a trigger assembly 18c that is operably coupled to and advances a cutting element 30 (see phantom) disposed within the end effector assembly 100. Once a tissue seal is formed, the user activates the trigger assembly 18c to separate the tissue along the tissue seal. Cutting element 30 may include a sharpened edge 32 for severing the tissue held between the jaw members 110 and 120 at the tissue sealing site.

Referring now to FIG. 1B, an open forceps 50 is depicted and includes end effector assembly 100 (similar to forceps 10) that is attached to a pair of elongated shaft portions 52a and 52b. Elongated shaft portions 52a and 52b have proximal ends 54a and 54b and distal ends 56a and 56b, respectively. The end effector assembly 100 includes jaw members 110 and 120 that attach to distal ends 56a and 56b of shafts 52a and 52b, respectively. The jaw members 110 and 120 are connected about pivot pin 55 that allows the jaw members 110 and 120 to pivot relative to one another from the first to second positions for treating tissue (as described above). The tissue contacting surfaces (e.g., seal plates) 112 and 122 are connected to opposing jaw members 110 and 120 and include electrical connections through or around the pivot pin 55.

Each shaft 52a and 52b includes a handle 57a and 57b disposed at the proximal end 54a and 54b thereof. Handles 57a and 57b facilitate movement of the shafts 52a and 52b relative to one another which, in turn, pivot the jaw members 110 and 120 from the open position wherein the jaw members 110 and 120 are disposed in spaced relation relative to one another to the clamping or closed position wherein the jaw members 110 and 120 cooperate to grasp tissue therebetween.

In an example embodiment, as depicted in FIG. 1B, a ratchet 58 (e.g., hemostat clamp) may be included for selectively locking the jaw members 110 and 120 relative to one another at various positions during pivoting. The ratchet 58 is configured to hold a specific, i.e., constant, strain energy in the shaft members 52a and 52b which, in turn, transmits a specific closing force to the jaw members 110 and 120. It is envisioned that the ratchet 58 may include graduations or other visual markings that enable the user to easily and quickly ascertain and control the amount of closure force desired between the jaw members 110 and 120.

With continued reference to FIG. 1B, forceps 50 is depicted having a cable 59 that connects the forceps 50 to a source of electrosurgical energy, e.g., generator 22. In a similar fashion to forceps 10, cable 59 of forceps 50 is internally divided within the shaft 52b to transmit electrosurgical energy through various electrical conductive paths to the components of the end effector assembly 100.

In embodiments, a switch assembly 53a may be configured to selectively provide electrical energy to the end effector assembly 100. More particularly, switch assembly 53a is configured to selectively supply electrical energy to tissue contacting surfaces 112 and 122 of jaw member 110 and 120, respectively. In addition to switch assembly 53a, forceps 50 may also include a trigger assembly 53b that is operably coupled to and advances a cutting element (not shown) disposed within shaft member 52b and end effector assembly 100. Once a tissue seal is formed, the user may activate trigger assembly 53b to separate the tissue along the tissue seal.

Jaw members 110 and 120 are configured to have a monolithic jaw configuration. Each monolithic jaw body 110, 120 is made of substantially all metal or any other suitable conductive material to facilitate conductance throughout the end effector assembly 100. Monolithic jaw members 110 and 120 include sealing surfaces 112 and 122 and each define a substantially wide cavity (e.g., cavity 114) that is configured to receive various embodiments of the presently disclose dielectric jaw inserts 200, 300, 400 and 500. Although both jaw members 110 and 120 may employ one or more dielectric inserts described herein, only one of the jaw members (e.g., jaw member 110) will be shown and described throughout the disclosure for simplification purposes.

Figure 2A:
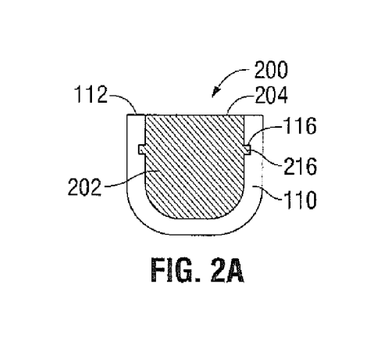
FIG. 2A is a cross-sectional view of an end effector assembly having a jaw insert in accordance with an embodiment of the present disclosure.
Figure 2B:
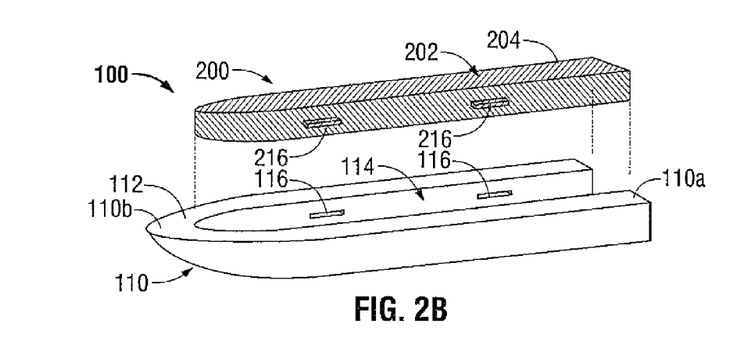
FIG. 2B is an exploded view of the end effector assembly of FIG. 2A.
Figure 2C:
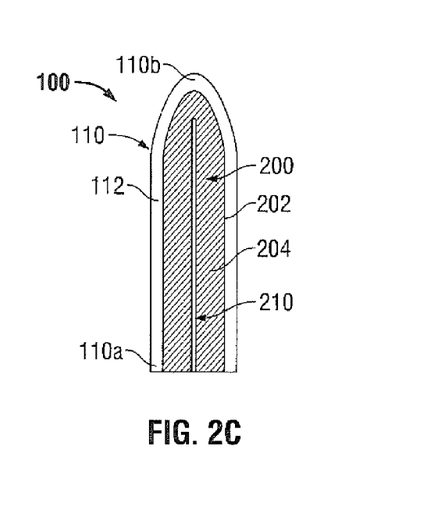
FIG. 2C is a top view of an end effector assembly of FIG. 2A having a cutting channel.

Referring now to FIGS. 2A-2C, a monolithic jaw member 110 is shown having a removable dielectric jaw insert 200. Jaw member 110 includes sealing surface 112 around a periphery thereof and is adapted to electrosurgically treat tissue that is grasped between jaw members 110 and 120 (as shown in FIG. 1). On an interior portion, monolithic jaw member 110 defines a cavity 114 that is configured to receive dielectric jaw insert 200. Dielectric jaw insert 200 includes a dielectric body 202 made of any suitable dielectric material, for example, but not limited to ceramic, plastic and epoxy. Dielectric jaw insert 200 also includes a tissue contacting surface 204 that allows tissue to be compressed therealong when tissue is grasped between jaw members 110, 120. To facilitate attachment to jaw member 110, dielectric jaw insert 200 may include one or more mechanical interfaces (e.g., tabs 216) that are configured to mechanically couple to corresponding one or more mechanical interfaces (e.g., grooves 116) disposed within or along an internal surface or periphery of cavity 114 of monolithic jaw 110.

The dielectric jaw insert 200 allows the jaw members 110 and 120 to modify the seal area and properly distribute the thermal mass of the end effector 100 during electrosurgical treatment of tissue. That is, a high concentration of thermal mass may be properly distributed through the jaw members 110, 120 by allowing the combination of materials in the jaw structure to be altered without compromising the size of the end effector assembly 100. In other words, a large end effector assembly 100 having large jaw members 110 may be utilized during an electrosurgical procedure but at the same time a small area of tissue sealing surface 112 may be utilized due to the displacement of dielectric insert 200.

As shown in FIG. 2A, sealing surface 112 of jaw member 110 and tissue contacting surface 204 of jaw insert 200 uniformally define an even surface. Other configurations are envisioned, for example, sealing surface 112 and tissue contacting surface 204 may be offset from each other.

In embodiments, dielectric jaw insert 200 may be coupled and secured to jaw member 110 via any suitable securement techniques known in the art. For example, securement of dielectric jaw insert 200 to monolithic jaw member 110 may be accomplished by stamping, by overmolding, by overmolding a stamped non-conductive jaw insert 200 and/or by overmolding a plastic injection molded jaw insert 200. All of these manufacturing techniques may be utilized to produce jaw member 110. Alternatively, jaw insert 200 may be secured to jaw member 110 via one or more types of mechanical interfaces. More particularly, jaw insert 200 may be secured to jaw member 110 via a press fit, fiction fit, bayonet fit, etc. In one particular embodiment, jaw insert 200 is secured to jaw member 110 via press fit.

FIG. 2C illustrates dielectric jaw insert 200 having a cutting channel 210 defined therethrough. As mentioned above, certain surgical procedures utilize a knife or cutting element 30 that is selectively movable within a pre-defined cutting channel 210 defined between jaw member 110 and 120. In this embodiment, cutting channel 210 is defined within jaw insert body 202. Since the cutting channel 210 is made of a dielectric material, conductive fluids residing within channel 210 (e.g., saline and blood) during treatment will remain substantially neutral and not conduct a charge from the tissue sealing surface. That is, during an electrosurgical procedure, the conductive fluids will not electrically react, thus the tissue seal cycle and/or quality will not be substantially affected by stray conductive fluids.

Figure 2D:
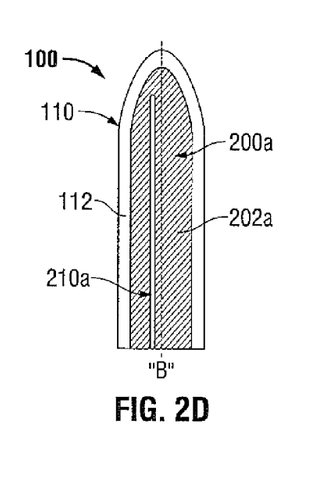
FIG. 2D is a top view of an end effector assembly of FIG. 2A having an offset cutting channel.

FIG. 2D illustrates jaw member 110 having a dielectric insert 200a that includes a dielectric body 202a. A longitudinal axis "B" is defined centrally and along jaw member 110. A cutting channel 210a may be defined laterally offset relative to longitudinal axis "B" at any portion of dielectric body 202a. For example, as shown in FIG. 2D, cutting channel 210a is laterally offset to one side of longitudinal axis "B." In this configuration, a cutting element 30 (as shown in FIG. 1) may be laterally offset, which, in turn, creates an offset cut along a complete tissue seal.

Figure 2E:
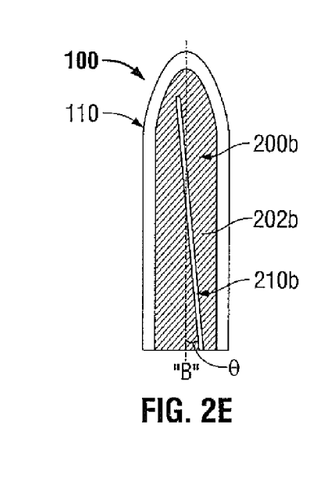
FIG. 2E is a top view of an end effector assembly similar to the end effector of FIG. 2A having an angled cutting channel.

FIG. 2E illustrates a jaw member 110 having a dielectric insert 200b that includes a dielectric body 202b. A longitudinal axis "B" is defined centrally and along jaw member 110. A cutting channel 210a may be defined angularly offset relative to longitudinal axis "B" at any angle "θ" of dielectric body 202a. For example, as shown in FIG. 2E, cutting channel 210a may be angularly offset and bisect longitudinal axis "B," defined by any angle "θ." In this configuration, a cutting element 30 (as shown in FIG. 1) may cut a completed tissue seal at any angular offset defined by angle "θ."

Figure 3A:
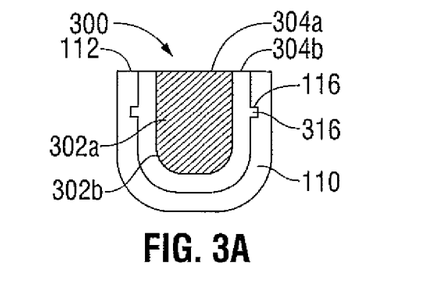
FIG. 3A is a cross-sectional view of another embodiment of an end effector assembly having a jaw insert in accordance with an embodiment of the present disclosure.
Figure 3B:
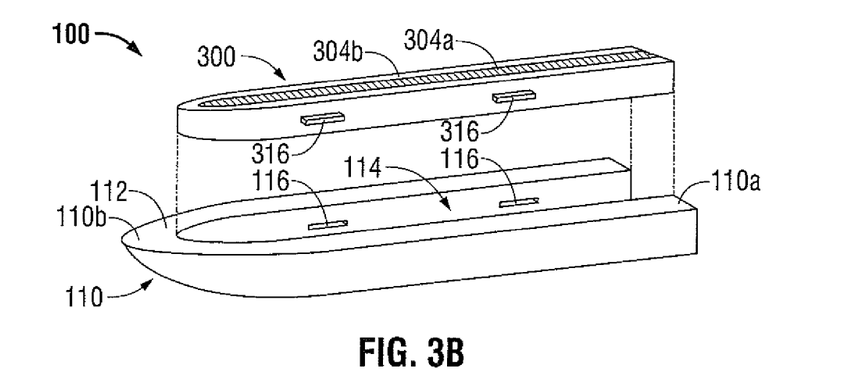
FIG. 3B is an exploded view of the end effector assembly of FIG. 3A.
Figure 3C:
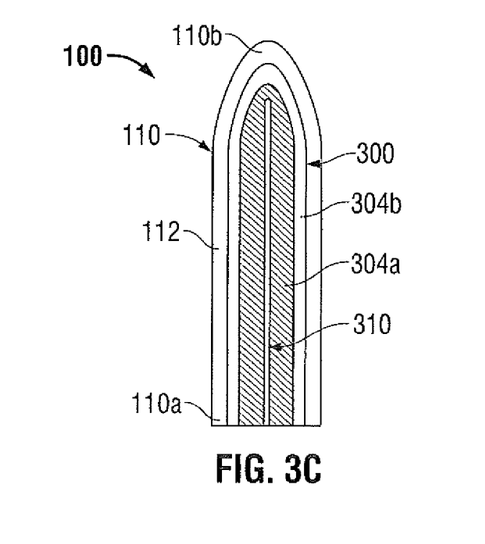
FIG. 3C is a top view of an end effector assembly of FIG. 3A having a cutting channel.

Referring now to FIG. 3A-3C, a monolithic jaw member 110 is shown having a removable hybrid jaw insert 300. As described above, jaw member 110 includes a sealing surface 112 around a periphery thereof and is adapted to electrosurgically treat tissue that is grasped between jaw members 110 and 120 (as shown in FIG. 1). On an interior portion, monolithic jaw member 110 defines a cavity 114 that is configured to receive jaw insert 300. Similar to dielectric jaw insert 200, hybrid jaw insert 300 includes a dielectric body 302a made of any suitable dielectric material, for example, but not limited to ceramic, plastic and epoxy. In addition to dielectric body 302a, hybrid jaw insert 300 includes a conductive body 302b that is disposed on the outside of dielectric body 302a.

Conductive body 302b may be made of any suitable conductive material, for example, but not limited to stainless steel. Hybrid jaw insert 300 also includes a dielectric tissue contacting surface 304a and a conductive tissue contacting surface 304b. Jointly, contacting surfaces 304a and 304b allow tissue to be compressed therealong when tissue is grasped between jaw members 110, 120. Similarly to dielectric jaw insert 200, hybrid jaw insert 300 includes tabs 316 that are configured to mechanically couple to grooves 116 disposed within cavity 114 of monolithic jaw 110 to facilitate attachment to jaw member 110. Any suitable set of mechanical interfaces may be used for this purpose.

In this configuration, when a greater thermal mass is required during a electrosurgical tissue treatment, dielectric insert 200 may be swapped with hybrid jaw insert 300, since hybrid jaw insert 300 provides additional conductive material 302b, which, in turn, provides additional electrosurgical energy to a tissue via sealing surfaces 112 and 304b.

As shown in FIG. 3A, sealing surface 112 of jaw member 110 and tissue contacting surfaces 304a and 304b of jaw insert 300 uniformally define an even surface. Other configurations are envisioned such that sealing surface 112 and tissue contacting surface 304 may be offset from each other. For example, dielectric tissue contacting surface 304a may be raised relative to surfaces 112 and 304b to provide a gap distance between jaw members 110 and 120 of about 0.001 inches to about 0.006 inches to facilitate vessel sealing. Alternatively, tissue surface 304a may include a series of raised projections or stop members that are dimensioned to provide a gap distance within the same range. A detailed discussion of the stop members is discussed in U.S. application Ser. No. 11/595,194, the contents of which is incorporated by reference herein.

Figure 4A:
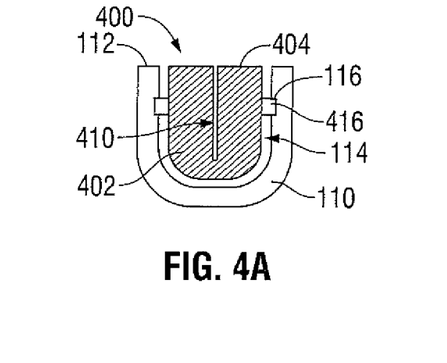
FIG. 4A is a cross-sectional view of yet another embodiment of an end effector assembly having a jaw insert in accordance with an embodiment of the present disclosure.
Figure 4B:
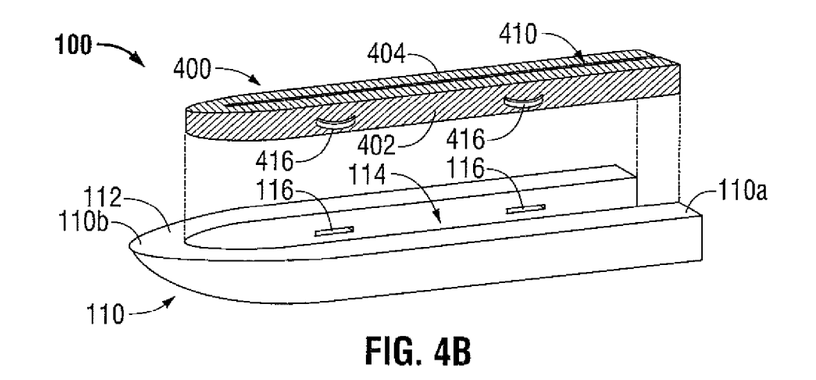
FIG. 4B is an exploded view of yet another embodiment of an end effector assembly including a jaw insert having a cutting channel in accordance with an embodiment of the present disclosure.
Figure 4C:
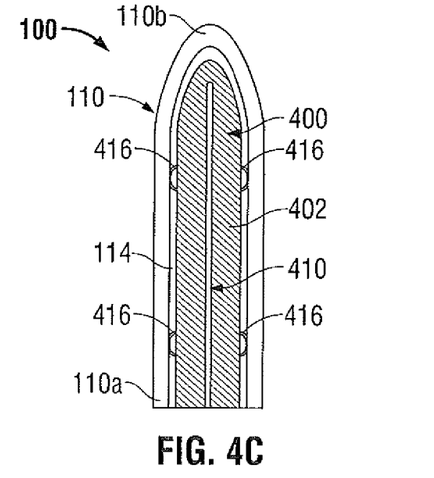
FIG. 4C is a top view of the end effector assembly of FIG. 4A.

Referring now to FIG. 4A-4C, a monolithic jaw member 110 is shown having a removable dielectric jaw insert 400. On an interior portion, monolithic jaw member 110 defines a cavity 114 that is configured to receive dielectric jaw insert 400. Dielectric jaw insert 400 includes a dielectric body made of any suitable dielectric material, for example, but not limited to ceramic, plastic and epoxy. Dielectric jaw insert 400 also includes a tissue contacting surface 402 that allows tissue to compress therealong when tissue is grasped between jaw members 110 and 120.

To facilitate attachment to jaw member 110, dielectric jaw insert 400 includes a plurality of biasing members 416 that are configured to mechanically couple to corresponding grooves 116 disposed within cavity 114 of monolithic jaw 110. Biasing members 416 allow dielectric jaw insert 400 to float within cavity 114 that may facilitate advancement and alignment of cutting element 30 (see FIG. 1). For example, if cutting element 30 is angularly offset, cutting channels 410 of jaw member 110 and the cutting channel (not shown) of jaw member 120 will not align properly. However, in accordance with the present embodiment, dielectric jaw inserts 400 of both jaw members 110 and 120 may reposition themselves, via biasing members 416 within cavity 114, such that cutting channels 410 of both jaw members 110 and 120 are properly aligned with each other to allow cutting element 30 to pass therethrough.

As shown in FIG. 4A-4C, sealing surface 112 of jaw member 110 and tissue contacting surface 404 of jaw insert 400 uniformally define an even surface. Other configurations are envisioned, for example, sealing surface 112 and tissue contacting surface 404 may be offset from each other.

Figure 5A:
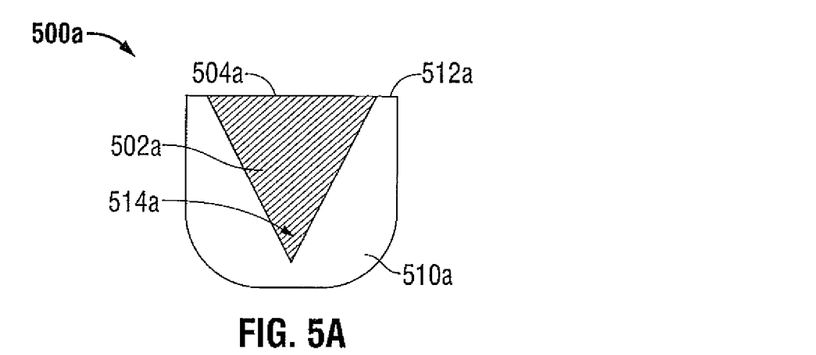
FIGS. 5A-5C are cross-sectional views of an end effector assembly including a jaw insert having various configurations.
Figure 5B:
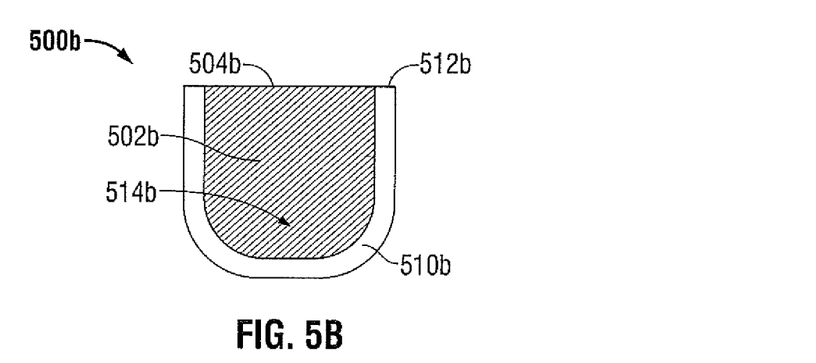
Figure 5C:
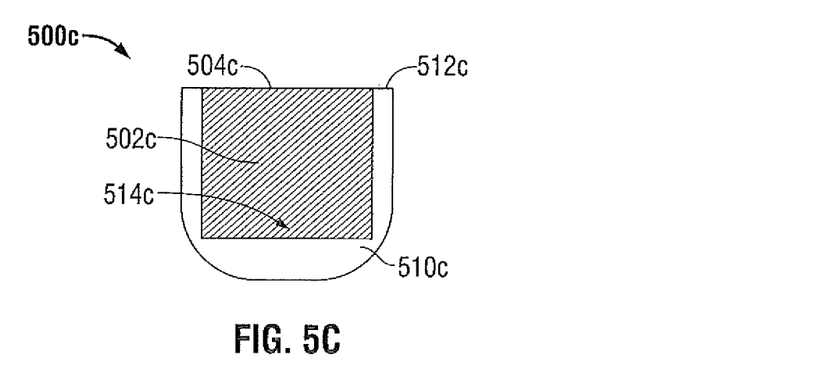

Referring now to FIG. 5A-5C, end effector assembly 500a, 500b, 500c includes a jaw member 510a, 510b, 510c having a sealing surface 512a, 512b, 512c disposed on an innerfacing surface thereof. FIG. 5A illustrates jaw member 510a including a jaw insert 502a having a v-shaped configuration that is disposed and coupled within a v-shaped cavity 514a defined by jaw insert 502a. FIG. 5B illustrates jaw member 510b including a jaw insert 502b having a u-shaped configuration that is disposed and coupled within a u-shaped cavity 514b defined by jaw insert 502b. FIG. 5C illustrates jaw member 510c including a jaw insert 502c having a square-shaped configuration that is disposed and coupled within a square-shaped cavity 514c defined by jaw insert 502c.

As similarly described with the aforementioned embodiments, a surface 504a, 504b, and 504c of dielectric jaw insert 502a, 502b, 502c and a sealing surface 512a, 512b, 512c of jaw member 510a, 510b, 510c may either be even or offset relative to each other.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed:

1. An end effector assembly for use with an electrosurgical instrument, the end effector assembly comprising:
   a pair of opposing first and second jaw members each having a tissue contacting surface, at least one of the first and second jaw members being monolithic and at least one jaw member moveable relative to the other from a first, open position to a second, closed position for grasping tissue, the at least one monolithic jaw member having a cavity defined therein; and
   a jaw insert selectively replaceable from within the cavity of the at least one monolithic jaw member, the jaw insert having a tissue contacting surface, at least a portion of the jaw insert including a dielectric material configured to allow selective reduction of the thermal mass of the at least one monolithic jaw member which, in turn, allows the selective regulation of energy between jaw members.

2. An end effector assembly according to claim 1, wherein the jaw insert defines a cutting channel therealong configured to receive a cutting element therealong.

3. An end effector assembly according to claim 1, wherein the jaw insert includes at least a portion of conductive material configured to conduct electrosurgical energy received from an electrosurgical energy source.

4. An end effector assembly according to claim 1, wherein the jaw insert is overmolded to the at least one monolithic jaw member.

5. An end effector assembly according to claim 1, wherein the jaw insert is made from one of plastic, ceramic and epoxy.

6. An end effector assembly according to claim 1, wherein the jaw insert includes at least one mechanical interface configured to cooperate with a corresponding mechanical interface to selectively position the jaw insert within the cavity.

7. An end effector assembly according to claim 6, wherein the at least one mechanical interface includes at least one biasing member.

8. An end effector assembly according to claim 1, wherein the tissue contacting surface of the at least one monolithic jaw member and the tissue contacting surface of the jaw insert are offset relative to one another.

9. An end effector assembly according to claim 1, wherein the tissue contacting surface of the jaw insert is raised relative to the tissue contacting surface of the monolithic jaw member to form a gap between the monolithic jaw member and the opposing jaw member in the range of about 0.001 inches to about 0.006 inches.

10. An end effector assembly according to claim 1, wherein the jaw insert is selectively removable from the cavity.

11. A method of manufacturing an end effector assembly for use with an electrosurgical instrument comprising the steps of:
   fabricating opposing jaw members, at least one jaw member being monolithic and having a cavity defined therein;
   fabricating a selectively replaceable jaw insert and at least a portion of the jaw insert including a dielectric material configured to allow selective reduction of the thermal mass of the monolithic jaw member which, in turn, allows the selective regulation of energy between jaw members; and
   positioning the jaw insert within the cavity of the monolithic jaw member.

12. A method according to claim 11, further comprising the step of:
   fabricating the jaw insert to define a cutting channel configured to receive a cutting element therealong.

13. A method according to claim 11, further comprising the step of:
   fabricating the jaw insert to include at least a portion of conductive material configured to conduct electrosurgical energy received from an electrosurgical energy source.

14. A method according to claim 11, further comprising the steps of overmolding and positioning the jaw insert within the cavity of the monolithic jaw member.

15. A method according to claim 11, wherein the jaw insert is made from one of plastic, ceramic and epoxy.

16. A method according to claim 11, further comprising the steps of:
   fabricating the jaw insert to include at least one mechanical interface that cooperates with a corresponding mechanical interface disposed within the cavity; and
   selectively positioning the jaw insert within the cavity.

17. A method according to claim 11, further comprising the step of:
   offsetting a tissue contacting surface of the monolithic jaw member from a tissue contacting surface of the jaw insert.

18. An end effector assembly for use with an electrosurgical instrument, the end effector assembly comprising:
   a pair of opposing first and second jaw members each having a tissue contacting surface, at least one of the first and second jaw members being monolithic and at least one jaw member moveable relative to the other from a first, open position to a second, closed position for grasping tissue, the at least one monolithic jaw member having a cavity defined therein; and
   a jaw insert selectively replaceable from within the cavity of the at least one monolithic jaw member, at least a portion of the jaw insert including a dielectric material configured to allow the thermal mass of the at least one monolithic jaw member which, in turn, allows the selective regulation of energy between jaw members, the jaw insert including at least one mechanical interface configured to cooperate with a corresponding mechanical interface to selectively position the jaw insert within the cavity.

19. An end effector assembly according to claim 18, wherein the at least one mechanical interface includes at least one biasing member.

20. An end effector assembly for use with an electrosurgical instrument, the end effector assembly comprising:
   a pair of opposing first and second jaw members each having a tissue contacting surface, at least one of the first and second jaw members being monolithic and at least one jaw member moveable relative to the other from a first, open position to a second, closed position for grasping tissue, the at least one monolithic jaw member having a cavity defined therein; and
   a jaw insert selectively replaceable from within the cavity of the at least one monolithic jaw member, the jaw insert having a tissue contacting surface, at least a portion of the jaw insert including a dielectric material configured to allow selective reduction of the thermal mass of the at least one monolithic jaw member which, in turn, allows the selective regulation of energy between jaw members, wherein the jaw insert further includes at least one mechanical interface extending laterally from the jaw insert and configured to engage a corresponding mechanical interface defined within the cavity such that the jaw insert may be removably inlayed into the cavity.

* * * * *